(12) United States Patent
Li et al.

(10) Patent No.: US 10,577,326 B1
(45) Date of Patent: *Mar. 3, 2020

(54) METHOD FOR PREPARING 2-CHLORO-6-TRICHLOROMETHYLPYRIDINE THROUGH LIQUID PHASE PHOTOCHLORINATION OF 2-METHYLPYRIDINE

(71) Applicant: Zhejiang Avilive Chemical Co., Ltd., Dongyang, Zhejiang (CN)

(72) Inventors: Huiyue Li, Zhejiang (CN); Keqiang Jin, Zhejiang (CN); Jiaquan Zhu, Zhejiang (CN)

(73) Assignee: Zhejiang Avilive Chemical, Co., Ltd., Dongyang (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/221,603

(22) Filed: Dec. 17, 2018

(30) Foreign Application Priority Data

Oct. 30, 2018 (CN) .......................... 2018 1 12723438

(51) Int. Cl.
| | | |
|---|---|---|
| *C07D 213/61* | (2006.01) | |
| *C07B 39/00* | (2006.01) | |
| *B01D 3/14* | (2006.01) | |
| *B01J 19/12* | (2006.01) | |

(52) U.S. Cl.
CPC ........... *C07D 213/61* (2013.01); *B01D 3/143* (2013.01); *B01J 19/123* (2013.01); *C07B 39/00* (2013.01); *B01J 2219/00033* (2013.01); *B01J 2219/00051* (2013.01); *B01J 2219/0875* (2013.01)

(58) Field of Classification Search
CPC ..................................................... C07D 213/61
USPC .......................................................... 546/345
See application file for complete search history.

(56) References Cited

PUBLICATIONS

U.S. Appl. No. 16/221,601, filed Dec. 17, 2018, Huiyue Li.
U.S. Appl. No. 16/221,600, filed Dec. 17, 2018, Huiyue Li.

*Primary Examiner* — Taofiq A Solola

(57) ABSTRACT

The present invention relates to a method for preparing 2-chloro-6-trichloromethylpyridine with product purity greater than or equal to 99.0% by using trifluoromethyl chlorobenzene as a solvent for reaction between 2-methylpyridine with chlorine gas, in which 2-methylpyridine and chlorine gas are used as starting materials, trifluoromethyl chlorobenzene is used as a solvent, 2-methylpyridine is prepared into a liquid raw material by using the solvent trifluoromethyl chlorobenzene, and the liquid raw material is continuously fed to perform liquid phase photochlorination reaction at temperature of 160-240° C. under irradiation of ultraviolet light to obtain 2-chloro-6-trichloromethylpyridine solution. Advantages: the selectivity of reaction for the production of 2-chloro-6-trichloromethylpyridine is improved, the content of components such as isomers and pentachloromethylpyridine in the crude product is decreased significantly, the crude product is easy to be purified to obtain the 2-chloro-6-trichloromethylpyridine product with purity greater than or equal to 99.0%, and the industrial production is facilitated; and secondly, not only can the reuse of the separated solvent in the preparation process of the 2,6-dichloropyridine product with purity greater than or equal to 99.0% be realized, but also the purposes of low pollution, low energy consumption and low cost in the preparation process are realized.

10 Claims, No Drawings

US 10,577,326 B1

METHOD FOR PREPARING 2-CHLORO-6-TRICHLOROMETHYLPYRIDINE THROUGH LIQUID PHASE PHOTOCHLORINATION OF 2-METHYLPYRIDINE

TECHNICAL FIELD

The present invention relates to method for preparing 2-chloro-6-trichloromethylpyridine with product purity greater than or equal to 99.0% by using trifluoromethyl chlorobenzene as a solvent for reaction between 2-methylpyridine and chlorine gas.

BACKGROUND ART

In CN101891675B titled "METHOD FOR PRODUCING 6-CHLORO-2-TRICHLOROMETHYLPYRIDINE", the method comprises the following steps: (1) preparing 2-methylpyridine into solution by Using part of a solvent, adding the residual solvent into a reaction kettle and feeding excessive chlorine gas, then continuously adding 2-methylpyridine solution into the reaction kettle to perform chlorination reaction at temperature of 130-205° C., and when the content of 6-chloro-2-dichloromethylpyridine is detected by GC to be smaller than or equal to 0.5%, stopping the reaction to obtain a 6-chloro-2-trichloromethylpyridine crude product; and (2) purifying the 6-chloro-2-trichloromethylpyridine crude product in step (1) by adopting a distillation method to obtain a 6-chloro-2-trichloromethylpyridine product, wherein the solvent is selected from a group consisting of halogenated or nitrated aromatic compounds, and the ratio of the total weight of the solvent to the weight of 2-triethylpyridine is 0.1-10:1.

The disadvantage of this method is that the selectivity of chlorination reaction to chloro-6-trichloromethylpyridine is not good, components such as isomers and pentachloromethylpyridine in chloride are too many to be separated through distillation, and the amount of produced tar is too high.

SUMMARY OF THE INVENTION

Purpose of design: in order to avoid the shortcomings mentioned in the background art, a method and production line using trifluoromethyl chlorobenzene as a solvent for reaction between 2-methylpyridine and chlorine gas, and photocatalytic reaction, are designed, which achieve the effects of good reaction selectivity of prepared 2-chloro-6-trichloromethylpyridine and high product purity greater than or equal to 99.0%, overcome the shortcomings in the preparation method mentioned in the background art, and achieve the purposes of low pollution, low energy consumption, low cost and easiness in batch preparation in industrial production.

Use of design of the present invention: 2-chloro-6-trichloromethylpyridine is a nitrogen fertilizer synergist which can selectively inhibit nitrification or denitrification in soil and improve the utilization rate of nitrogen fertilizer. It is codenamed CP which contains 6% of nitrogen and is white crystal solid. Now it is widely used abroad and has the best effect. Our country has also done experiments on many crops, which proves that it has a certain yield-increasing effect. Its application amount is about 1% of the application amount of pure nitrogen. When its concentration in the soil is 1-10 mg/kg, it has a significant inhibition effect on soil nitrification. Its validity period is about 30 days. For rice, maize, wheat, sorghum, cotton, rape and other crops, it can generally increase production by about 10%, and reduce the amount of nitrogen fertilizer application amount by ⅓-½, improve the utilization rate of nitrogen fertilizer and reduce agricultural non-point source pollution.

In order to realize the purpose of design of the present invention, the present invention designs a method for performing liquid phase photochlorination reaction at temperature of 160-240° C. under irradiation of ultraviolet light, by using 2-methylpyridine and chlorine gas as starting materials, using trifluoromethyl chlorobenzene as a solvent, and continuously feeding raw materials, which is a main technical feature of the present invention. The purpose of such design is as follow: in industrial production, reaction materials of a previous batch are reserved in the photochlorination reactor, 2-methylpyridine, chlorine gas and trifluoromethyl chlorobenzene are continuously added into the photochlorination reactor according to proportions to perform photochlorination reaction, and the chlorination solution overflows into a collection tank, such that the selectivity of reaction for production of 2-chloro-6-trichloromethylpyridine can be improved, components such as isomers and pentachloromethylpyridine in the crude product can the decreased significantly, and at the same time the situations of excessive temperature, coking and carbonization caused by heat emitted in reaction can the avoided. Before the liquid phase photochlorination reaction, an ultraviolet light lamp in the chlorination reactor is turned on and chlorine gas is fed into the photochlorination reactor. At the same time, 2-methylpyridine and trifluoromethyl chlorobenzene are mixed according to the proportions and then the mixture is added into the photochlorination reactor by using a peristaltic pump to perform continuous liquid phase photochlorination reaction under irradiation of light. Since the solvent in an amount greater than 15% of the volume of the photochlorination reactor is added at the first start-up of the photochlorination reactor, the solvent used as the diluent of the reaction materials can improve the selectivity of reaction for the production of 2-chloro-6-trichloromethylpyridine, the content of impurities such as isomers and pentachloromethylpyridine in the crude product is significantly reduced, and at the same time the chlorination reaction is slowed down, the intensity of heat emission in reaction is reduced, the vaporization of the solvent takes away a large amount of reaction heat, and the situation of coking of materials caused by excessive local temperature of the reaction materials is avoided, and the coking rate is significantly reduced. More importantly, not only can the yield be improved, but also the preparation efficiency of the 2-methylpyridine product with purity greater than or equal to 99.0% is enabled to be more scientific and simple, the intermediate link in, the background art is avoided, and unexpected technical effects are achieved, which are specifically reflected as follows:

Comparative Test Data of Processes for Preparing 2-chloro-6-trichloromethylpyridine

| Test comparison item | Preparation method | Coking rate | Yield of product | Selectivity of product | Selectivity of isomer | Selectivity of Pentachloromethylpyridine | Amount of produced waste residues (t) | Treatment cost of waste residues |
|---|---|---|---|---|---|---|---|---|
| Background art | Liquid phase thermal chlorination | 30% | 63% | 64% | 2% | 4% | 186 kg | 930 CNY/t |
| Present invention | Liquid phase photochlorination | 27% | 67% | 71.7% | 0.5% | 0.8% | 160 kg | 800 CNY/t |

Technical solution: a method for preparing 2 chloro-6-trichloromethylpyridine through liquid phase photochlorination of 2-methylpyridine, in which 2-methyl pyridine and chlorine gas were used as starting materials, trifluoromethyl chlorobenzene was used as a solvent, 2-methylpyridine was prepared into a liquid raw material by using the solvent trifluoromethyl chlorobenzene, and the liquid raw material was contentiously, fed to perform liquid phase photochlorination reaction at temperature of 160-240° C. under irradiation of ultraviolet light to obtain 2-chloro-6-trichloromethylpyridine solution.

Compared with the background art, the selectivity of reaction for the production of 2-chloro-6-trichloromethylpyridine is improved, the content of components such as isomers and pentachloromethylpyridine in the crude product is decreased significantly, the crude product is easy to be purified to obtain the 2-chloro-6-trichloromethylpyridine product with purity greater than or equal to 99.0%, and the industrial production is facilitated; and secondly, not only can the reuse of the separated solvent in the preparation process of the 2,6-dichloropyridine product with purity greater than or equal to 99.0% be realized, but also the purposes of low pollution, low energy consumption and low cost in the preparation process are realized.

DESCRIPTION OF THE EMBODIMENTS

Embodiment 1

A method for preparing 2-chloro-6-trichloromethylpyridine through liquid phase photochlorination of 2-methylpyridine in which 2-methylpyridine and chlorine gas were used as starting materials, trifluoromethyl chlorobenzene was used as a solvent, 2-methylpyridine was prepared into a liquid raw material by using the solvent trifluoromethyl chlorobenzene, and the liquid raw material was continuously fed to perform liquid phase photochlorination reaction at temperature of 160-240° C. under irradiation of ultraviolet light to obtain chlorination solution containing 2-chloro-6-trichloromethylpyridine.

In this embodiment, the weight ratio of 2-methylpyridine to the solvent was 1:0.2-4. At the start of chlorination reaction, a certain amount of solvent was added into a chlorination reactor in advance, heating was performed to increase temperature to above 150° C., then Chlorine gas was continuously feed, at the same time the mixture of 2-methylpyridine and the solvent was continuously dripped according to proportions, and reaction solution was continuously discharged into a material collector or a crude distillation kettle. At the start of chlorination reaction, the amount of the added solvent was 15-80% of the volume of the reactor and the amount of fed chlorine gas was 3-7 times the weight of 2-methylpyridine. The ultraviolet light for irradiation came from an ultraviolet light source or blue light source with a wavelength of 254-400 nm. The solvent included, but not limited to, trifluoromethyl monochlorobenzene, trifluoromethyl dichlorobenzene and trifluoromethyl trichlorobenzene.

Test Data of Conditions (Chlorination Materials) for Liquid Phase Photochlorination of 2-Methylpyridine

| Reaction temperature (° C.) | 160° C. | 180° C. | 195° C. | 205° C. | 240° C. |
|---|---|---|---|---|---|
| Weight of chlorination solution (g) | 2835.65 | 2826.35 | 2823.44 | 2786.32 | 2743.72 |
| Content of solvent (%) | 51.44 | 51.62 | 51.68 | 52.39 | 53.24 |
| Content of 2-chloro-6-trichloromethylpyridine (%) | 34.10 | 38.21 | 39.96 | 35.86 | 30.55 |
| Content of isomer (%) | 0.15 | 0.14 | 0.16 | 0.17 | 0.11 |
| Content of pentachloromethylpyridine(%) | 0.25 | 0.27 | 0.30 | 0.79 | 0.24 |

Embodiment 2

On the basis of embodiment 1, 2-methylpyridine and chlorine gas were used as starting materials, trifluoromethyl chlorobenzene was used as a solvent, 2-methylpyridine was prepared into a liquid raw material by using the solvent trifluoromethyl chlorobenzene, the liquid raw material was continuously fed to perform liquid phase photochlorination reaction at temperature of 160-240° C. under irradiation of ultraviolet light to obtain 2-methylpyridine chlorination solution, the chlorination solution was subjected to crude distillation, then tar and high-boiling-point substances were separated, and the obtained distillate was a 2-chloro-6-trichloromethylpyridine crude product containing the solvent.

Test Data of Conditions (Crude Distillation
Materials) for Liquid Phase Photochlorination of
2-Methylpyridine

| Reaction temperature (° C.) | 160° C. | 180° C. | 195° C. | 205° C. | 240° C. |
|---|---|---|---|---|---|
| Weight of crude distillate (g) | 2571.05 | 2539.67 | 2519.74 | 2456.38 | 2390.22 |
| Content of solvent (%) | 53.90 | 54.58 | 55.01 | 56.46 | 58.05 |
| Content of 2-chloro-6-trichloromethlpyridine (%) | 37.61 | 42.52 | 44.77 | 40.68 | 35.06 |
| Content of isomer (%) | 0.17 | 0.16 | 0.18 | 0.19 | 0.13 |
| Content of pentachloro-methylpyridine (%) | 0.28 | 0.30 | 0.34 | 0.33 | 0.28 |
| Weight of tar (g) | 129.29 | 153.01 | 171.08 | 200.66 | 227.70 |
| Coking rate (%) | 19.89 | 23.54 | 26.32 | 30.87 | 35.03 |

Embodiment 3

On the basis of embodiment 1 and embodiment 2, 2-methylpyridine and chlorine gas were used as starting materials, trifluoromethyl chlorobenzene was used as a solvent, 2-methylpyridine was prepared into a liquid raw material by using the solvent trifluoromethyl chlorobenzene, the liquid raw material was continuously fed to perform liquid phase photochlorination reaction at temperature of 160-240° C. under irradiation of ultraviolet light to obtain 2-chloro-6-trichloromethylpyridine solution, the 2-Chloro-6-trichloromethylpyridine solution was subjected to crude distillation, then tar and high-boiling-point substances were separated, the obtained distillate was a 2-chloro-6-trichloromethylpyridine crude product containing the solvent, and the crude product was purified by adopting a rectification method to obtain a 2-chloro-6-trichloromethylpyridine product with purity greater than or equal to 99.0%.

Test Data of Conditions (Rectification Separation)
for Liquid Phase Photochlorination of
2-Methylpyridine

| Reaction temperature (° C.) | 160° C. | 180° C. | 195° C. | 205° C. | 240° C. |
|---|---|---|---|---|---|
| Weight of product (g) | 954.86 | 1065.12 | 1104.90 | 980.59 | 812.11 |
| Content of product (%) | 99.01 | 99.02 | 99.16 | 98.96 | 98.97 |
| Yield of product (%) | 56.66 | 65.44 | 67.98 | 60.21 | 49.87 |

The rectification purification method was to separate and purify 2-chloro-6-trichloromethylpyridine from the 2-chloro-6-trichloromethylpyridine rude product containing the solvent to obtain the product with purity greater than or equal to 99.0% and the solvent with purity greater than or equal to 95.0%, wherein the solvent was reused.

Embodiment 4

On the basis of embodiment 2,2-methylpyridine and chlorine gas were used as starting materials, trifluoromethyl chlorobenzene was used as a solvent, 2-methylpyridine was prepared into a liquid raw material by using the solvent trifluoromethyl chlorobenzene, the liquid raw material was continuously fed to perform liquid phase photochlorination reaction at temperature of 160-240° C. under irradiation of ultraviolet light to obtain 2-chloro-6-trichloromethylpyridine solution, the 2-chloro-6-trichloromethylpyridine solution was subjected to crude distillation, then tar and high-boiling-point substances were separated, and the obtained distillate was a 2-chloro 6-trichloromethylpyridine crude product containing the solvent.

The 2-chloro-6-trichloromethylpyridine crude product containing the solvent was separated by adopting cooling crystallization, the solvent was removed, and then 2 chloro-6-trichloromethylpyridine with purity greater than or equal to 99.0% was obtained. The crystallization separation purification method was to separate from 2-chloro-6-trichloromethylpyridine crude product containing the solvent through cooling crystallization and remove the solvent through distillation to obtain a 2-chloro-6-trichloromethylpyridine product with purity greater than or equal to 99.0% and the solvent with purity greater than or equal to 95.0%, wherein the solvent was reused; and the solvent and part of the product were recovered from the crystallization mother solution through a rectification method.

Test Data of Conditions (Crystallization Separation)
for Liquid Phase Photochlorination
2-Methylpyridine

| Reaction temperature (° C.) | 160° C. | 180° C. | 195° C. | 205° C. | 240° C. |
|---|---|---|---|---|---|
| Weight of product (g) | 935.76 | 1043.81 | 1082.80 | 960.97 | 795.86 |
| Content of product (%) | 99.03 | 99.07 | 99.01 | 99. 11 | 99.05 |
| Yield of product (%) | 57.50 | 64.16 | 66.52 | 59.10 | 48.91 |

Embodiment 5

The liquid phase photochlorination method in the embodiments may also be implemented intermittently.
Description will be made through examples:

Example 1

1. 120 g of trifluoromethyl trichlorobenzene was added as a base material into a 500 ml overflow flask, temperature was increased to 150° C., then chlorine gas was fed at 250 ml/min, an ultraviolet light lamp was turned on, and temperature was continuously increased to 160° C.

2. After temperature was increased to 160° C., 30% 2-methylpyridine trifluoromethyl trichlorobenzene solution was dripped, the dripping speed was controlled to be 0.4 ml/min, then the temperature was increased gradually with reaction, and finally the reaction temperature was controlled to be 160-240° C.

3. After the reaction solution rose to an overflow opening, the reaction solution began to flow out to a 2000 ml collection bottle, and pyridine was continuously dripped until the raw material solution (350 g of pyridine and 1397 g of trifluoromethyl trichlorobenzene) was fully dripped.

4. After reaction was completed, reduced pressure distillation was performed to the taken-out reaction solution until no distillate was evaporated obviously. The residual solution was tar and weighed.

5. The evaporated distillate was heated and melted, then temperature was slowly decreased to below 10° C. under stirring, then stirring at heat preservation was continuously performed for 1 h below 10° C. until the product was fully precipitated, and then filtration was performed.

6. Filter cake rectification was performed to separate the solvent and other components to Obtain the 2-chloro-6-trichloromethylpyridine product with purity greater than or equal to 99.0%. The filtrate was subjected to rectification separation to recover the solvent and other components.

Test Data of Conditions for Liquid Phase Photochlorination of 2-Methylpyridine (Different Temperature)

| Reaction temperature (° C.) | 160° C. | 180° C. | 195° C. | 205° C. | 240° C. |
|---|---|---|---|---|---|
| Weight of product (g) | 935.76 | 1043.81 | 1082.80 | 960.97 | 795.86 |
| Content of product (%) | 99.03 | 99.07 | 99.01 | 99.11 | 99.05 |
| Coking rate (%) | 12.32 | 14.61 | 14.78 | 15.73 | 20.1 |
| Yield of product (%) | 57.50 | 64.16 | 66.52 | 59.10 | 48.91 |

Example 2

1. 120 g of trifluoromethyl trichlorobenzene was added as a base material into a 500 ml overflow flask, temperature was increased to 150° C., then chlorine gas was fed at 150-350 ml/min, an ultraviolet light lamp was turned on, and temperature was continuously increased to 160° C.

2. After temperature was increased to 160° C. 30% 2-methylpyridine trifluoromethyl trichlorobenzene solution was dripped, the dripping speed was controlled to be 0.4 ml/min, then the temperature was increased gradually with reaction, and finally the reaction temperature was controlled to be 195° C.

3. After the reaction solution rose to an overflow opening, the reaction solution began to flow oat to a 2000 ml collection bottle, and pyridine was continuously dripped until the raw material solution (650 g of pyridine and 1397 g of trifluoromethyl trichlorobenzene) was fully dripped.

4. After reaction was completed, reduced pressure distillation was performed to the taken-out reaction solution until no distillate was evaporated obviously. The residual solution was tar and weighed.

5. The crude distillate was rectified to remove the solvent and other components to obtain the 2-chloro-6-trichloromethylpyridine product with purity greater than or equal to 99.0%.

Test Data of Conditions for Liquid Phase Photochlorination of 2-Methylpyridine (Different Chlorine Gas Amounts)

| Chlorine. gas speed (ml/min) | 150 | 200 | 250 | 300 | 350 |
|---|---|---|---|---|---|
| Weight of product (g) | 881.90 | 1004.53 | 1104.90 | 1107.06 | 1106.76 |
| Content of product (%) | 99.05 | 99.04 | 99.16 | 99.01 | 99.08 |
| Coking rate (%) | 35.38 | 30.69 | 26.32 | 25.63 | 25.47 |
| Yield of product (%) | 54.20 | 61.73 | 67.98 | 68.01 | 68.04 |

Example 3

1. 120 g of trifluoromethyl trichlorobenzene was added as a base material into a 500 ml overflow flask, temperature was increased to 150° C., then chlorine gas was fed at 250 ml/min, an ultraviolet light lamp was turned on, and temperature was continuously increased to 160° C.

2. After temperature was increased to 160° C., 20-80% 2-methylpyridine trifluoromethyl trichlorobenzene solution was dripped, the dripping speed was controlled to be 0.6-0.2 ml/min, then the temperature was increased gradually with reaction, and finally the reaction temperature was controlled to be 195° C.

3. After the reaction solution rose to an overflow opening, the reaction solution began to flow out to a 2000 ml collection bottle, and pyridine was continuously dripped until the raw material solution (650 g of pyridine and 2480-42.5 g of trifluoromethyl trichlorobenzene) was fully dripped.

Other operation steps are the same as that in example 2.

Test Data of Conditions for Liquid Phase Photochlorination of 2-Methylpyridine (Different Solvent Proportions)

| 2-methyipyridine concentration (%) | 20 | 30 | 50 | 65 | 80 |
|---|---|---|---|---|---|
| Weight or product (g) | 1142.29 | 1104.90 | 1064.95 | 987.43 | 951.86 |
| Content of product (%) | 99.06 | 99.16 | 99.02 | 99.09 | 99.00 |
| Coking rate (%) | 20.89 | 26.32 | 27.77 | 30.56 | 32.81 |
| Yield of product (%) | 70.21 | 67.98 | 65.43 | 60.71 | 58.47 |

It needs to be understood that, although the above-mentioned embodiments give more detailed descriptions of the design concept of the present invention, these descriptions are only simple descriptions of the design concept of the present invention, instead of limitations to the design concept of the present invention, and any combination, addition or modification that does not go beyond the design concept of the present invention shall fall within the protection scope of the present invention.

What is claimed is:

1. A method for preparing 2-chloro-6-trichloromethylpyridine through liquid phase photochlorination of 2-methylpyridine, wherein 2-methylpyridine and chlorine gas are used as starting materials, trifluoromethyl chlorobenzene is used as a solvent, 2-methylpyridine is prepared into a liquid raw material by using the solvent trifluoromethyl chlorobenzene, and the liquid raw material is continuously fed to perform liquid phase photochlorination reaction at temperature of 160-240° C. under irradiation of ultraviolet light to obtain 2-chloro-6-trichloromethylpyridine solution.

2. The method for preparing 2-chloro-6-trichloromethylpyridine through liquid phase photochlorination of 2-methylpyridine according to claim 1, wherein 2-methylpyridine and chlorine gas are used as starting materials, trifluoromethyl chlorobenzene is used as a solvent, 2-methylpyridine is prepared into a liquid raw material by using the solvent trifluoromethyl chlorobenzene, the liquid raw material is continuously fed to perform liquid phase photochlorination reaction at temperature of 160-240° C. under irradiation of ultraviolet light to obtain 2-chloro-6-trichloramethylpyridine solution, the 2-chloro-6-trichloramethylpyridine solution is subjected to crude distillation, then tar and high-boiling-point substances are separated, and the obtained distillate is a 2-chloro-6-trichloromethylpyridine crude product containing the solvent.

3. The method for preparing 2-chloro-6-trichloromethylpyridine through liquid phase photochlorination 2-methylpyridine according to claim 1, wherein 2-methylpyridine and chlorine gas are used as starting materials, trifluoromethyl chlorobenzene is used as a solvent, 2-methylpyridine is prepared into a liquid raw material by using the solvent trifluoromethyl chlorobenzene, the liquid raw material is continuously fed to perform liquid phase photochlorination reaction at temperature of 160-240° C. under irradiation of ultraviolet light to obtain 2-chloro-6-trichloromethylpyridine solution, the 2-chloro-6-trichloromethylpyridine solution is subjected to crude distillation, then tar and high-boiling-point substances are separated, the obtained distillate is a 2-chloro-6-trichloromethylpyridine crude product containing the solvent, the 2-chloro-6-trichloromethylpyridine crude product containing the solvent is separated adopting cooling crystallization, the solvent is removed, and then 2-chloro-6-trichloromethylpyridine with purity greater than or equal to 99.0% is obtained, or 2-chloro-6-trichloromethylpyridine containing the solvent is purified by adopting a rectification method to obtain 2-chloro-6-trichloromethylpyridine with purity greater than or equal to 99.0%.

4. The method for preparing 2-chloro-6-trichloromethylpyridine through liquid phase photochlorination of 2-methylpyridine according to claim 1, wherein the weight ratio of 2-methylpyridine to the solvent is 1:0.2-4.

5. The method for preparing 2-chloro-6-trichloromethylpyridine through liquid phase photochlorination of 2-methylpyridine according to claim 1, wherein, at the start of chlorination reaction, a certain amount of solvent is added into a chlorination reactor in advance, heating is performed to increase temperature to above 150° C., then chlorine gas is continuously fed, at the same time the mixture of 2-methylpyridine and the solvent is continuously dripped according to proportions, and reaction solution is continuously discharged into a material collector or a crude distillation kettle.

6. The method for preparing 2-chloro-6-trichloromethylpyridine through liquid phase photochlorination of 2-methylpyridine according to claim 5, wherein, at the start of chlorination reaction, the amount of the added solvent is 15-80% of the volume of the reactor and the amount of fed chlorine gas is 3-7 times the weight of 2-methylpyridine.

7. The method for preparing 2-chloro-6-trichloromethylpyridine through liquid phase photochlorination of 2-methylpyridine according to claim 1, wherein the rectification purification method is to separate and purify 2-chloro-6-trichloromethylpyridine from 2-methylpyridine chloride containing the solvent to obtain the product with purity greater than or equal to 99.0% and the solvent with purity greater than or equal to 95.0%, wherein the solvent is reused.

8. The method for preparing 2-chloro-6-trichloromethylpyridine through liquid phase photochlorination of 2-methylpyridine according to claim 1, wherein the crystallization separation purification method is to separate from 2-chloro-6-trichloromethylpyridine chloride containing the solvent through cooling crystallization and remove the solvent to obtain 2-chloro-6-trichloromethylpyridine with purity greater than or equal to 99.0% and the solvent with purity greater than or equal to 95.0%, wherein the solvent is reused; and the solvent and part of the product are recovered from the crystallization mother solution through a rectification method.

9. The method for preparing 2-chloro-6-trichloromethylpyridine through liquid phase photochlorination of 2-methylpyridine according to claim 1, wherein the ultraviolet light for irradiation comes from an ultraviolet light source or blue light source with a wavelength of 254-400 nm; and the solvent includes, but not limited to, trifluoromethyl monochlorobenzene, trifluoromethyl dichlorobenzene and trifluoromethyl trichlorobenzene.

10. The method for preparing 2-chloro-6-trichloromethylpyridine through liquid phase photochlorination of 2-methylpyridine according to claim 1, wherein the liquid phase photochlorination method may also be implemented intermittently.

* * * * *